United States Patent
Pisharodi

(10) Patent No.: US 8,317,843 B2
(45) Date of Patent: Nov. 27, 2012

(54) MULTI-AXIS CONNECTION AND METHODS FOR INTERNAL SPINAL STABILIZERS

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 858 days.

(21) Appl. No.: 11/827,222

(22) Filed: Jul. 11, 2007

(65) Prior Publication Data
US 2009/0018557 A1 Jan. 15, 2009

(51) Int. Cl.
*A61B 17/80* (2006.01)
(52) U.S. Cl. .......................... 606/287; 606/281; 606/291
(58) Field of Classification Search ................... 606/280, 606/286, 287, 289, 291, 301, 305, 319, 281
See application file for complete search history.

(56) References Cited

U.S. PATENT DOCUMENTS

| | | | |
|---|---|---|---|
| 5,954,722 A * | 9/1999 | Bono ............................ | 606/281 |
| 2003/0208204 A1* | 11/2003 | Bailey et al. ..................... | 606/69 |
| 2003/0225409 A1* | 12/2003 | Freid et al. ....................... | 606/69 |
| 2004/0049197 A1* | 3/2004 | Barbera Alacreu ............. | 606/73 |
| 2004/0167526 A1* | 8/2004 | Jackson ............................ | 606/73 |
| 2004/0267264 A1* | 12/2004 | Konieczynski et al. ......... | 606/73 |
| 2006/0149251 A1* | 7/2006 | Ziolo et al. ...................... | 606/69 |
| 2006/0161157 A1* | 7/2006 | Mosca et al. .................... | 606/69 |
| 2006/0235399 A1* | 10/2006 | Carls et al. ...................... | 606/69 |
| 2006/0276793 A1 | 12/2006 | Berry | |
| 2007/0073297 A1* | 3/2007 | Reynolds ......................... | 606/69 |
| 2008/0103503 A1* | 5/2008 | Roux et al. ....................... | 606/69 |
| 2008/0234748 A1* | 9/2008 | Wallenstein et al. ........... | 606/289 |

FOREIGN PATENT DOCUMENTS

| | | |
|---|---|---|
| DE | 19858889 | 6/2000 |
| FR | 2827150 | 7/2001 |
| FR | 2880929 | 7/2006 |
| FR | 2907663 | 10/2006 |
| WO | WO 0062692 | 10/2000 |

OTHER PUBLICATIONS

European Office Action dated Sep. 1, 2011 for European counterpart application No. EP08780065.2.

* cited by examiner

*Primary Examiner* — Thomas Barrett
*Assistant Examiner* — Michael T Schaper
(74) *Attorney, Agent, or Firm* — D'Ambrosio & Menon, PLLC; Usha Menon

(57) ABSTRACT

A multi-axis connection for transferring load from the vertebrae of a patient to a plate extending from one vertebra to another vertebra when affixed to the respective vertebrae by screws extending through holes in the plate at the level of the respective vertebrae, each screw being oriented at any of a plurality of angles relative to the plate. The threaded shank of each screw is screwed into the vertebral body and the head is positioned in the central portion of the hole, the hole being defined by an aperture, an opening through which the screw extends, and the central portion between aperture and opening. The diameter of the head is larger than the aperture of the hole in the plate and is provided with a screw thread that engages the smaller diameter aperture of the hole to pull the head into the central portion of the hole when the screw is rotated, the head of the screw being retained within the hole by the smaller diameter aperture and the opening of the hole.

12 Claims, 3 Drawing Sheets

MULTI-AXIS CONNECTION AND METHODS FOR INTERNAL SPINAL STABILIZERS

BACKGROUND OF THE INVENTION

The present invention relates to multi-axis apparatus and methods for internal spinal fixation. In more detail, the present invention relates to a connection for an internal spinal fixation system, and a method of stabilizing, or fixing, the spine, utilizing multiple axes for transferring load from the patient's spinal column to the stabilizer.

Treatment of a damaged or diseased intervertebral disk continues to be a challenging field of medicine. The classical treatment for a damaged or diseased disk is removal of all or a portion of the disk from between the vertebrae. However, removing the disk increases the instability of the spine. If only a portion of the disk is removed, the intervertebral disk space is commonly filled with a bone plug or prosthetic device and the space around the plug or the implant is packed with bone chips to promote fusion of the adjacent disks, thereby increasing spinal stability. However, depending upon the particular pathology of the patient, partial diskectomy and fusion is not always indicated and problems relating to the failure of the bone chips to fuse and other complications of this surgery are well documented.

It is also known to use internal spinal stabilizers to address certain pathologies involving instability of the spinal column. Such stabilizers are utilizing in the thoracic and lumbar regions of the spine where the approach is from the patient's dorsal aspect. In the cervical region, a ventral approach (from the patient's front) presents the opportunity to use an internal stabilizer which is not nearly as affected by the problem of effective load transfer from vertebrae to stabilizer through the screw attaching the stabilizer to the vertebrae that characterize internal stabilizers implanted (dorsally) in the thoracic and lumbar region. Although not limited to this application, a spinal stabilizer incorporating the multi-axis connection of the present invention is intended for use in stabilizing the spinal column in the cervical region where effective load transfer may not be as complicated as with stabilizers intended for use in the thoracic and lumbar regions of the spine, but where load transfer is just as critical such that the stabilizer must be capable of being securely affixed to the vertebrae adjacent the diseased or damaged disk. To do so, the screws that affix the stabilizer plate to the vertebrae must be angled (relative to the surface of the plate) as required by the shape and size of the vertebrae, the normal curvature of the spinal column, the number of vertebrae to be stabilized, the spacing between vertebrae, the pathology of the patient's spinal column, and the many other factors encountered by the surgeon that are unique to each and every patient and each and every surgery. The multi-axis connection is also adaptable for use in an internal spinal stabilizer that is affixed to the thoracic or lumbar regions of the spine by dorsal approach.

It is, therefore, an object of the present invention to improve the interface between the screw and the plate in those spinal stabilizers which are affixed to the vertebrae by a screw and in which the screws are angled and/or spaced at varying intervals.

Another object of the present invention is to provide flexibility of placement, angulation, spacing, and screw height for accommodating the screws that are utilized to affix the plate of such stabilizers to the vertebrae.

Another object of the present invention is to provide a multiple-axis connection for an internal spinal stabilizer that allows the screw to be angled relative to the plate and in accordance with the particular circumstances of the patient's anatomy and pathology but which still resists movement of the screw relative to the plate after the stabilizer has been affixed to the vertebrae by locking the head of the screw into the plate.

Yet another object of the present invention is to provide an internal spinal stabilizer incorporating a multi-axis connection that locks the head of the screw utilized for affixing the plate comprising the stabilizer to the plate so as to resist relative movement between the plate and the screw but which also allows the screw to be removed from the plate as may be needed for effective load transfer from the patient's vertebrae to the stabilizer when affixed to the vertebrae or in the event the stabilizer must be removed or replaced at a later date.

Another object of the present invention is to provide a method of transferring load from a patient's spinal column to the plate of a spinal stabilizer by screws extending from the plate into the vertebrae at any of a plurality of angles while retaining the screw to the plate.

Other objects, and the many advantages, of the present invention will be made clear to those skilled in the art by the following description of the preferred embodiments thereof.

SUMMARY OF THE INVENTION

These, and other, objects of the present invention to be made clear by the following detailed description of the invention, are met by providing a connection between the plate of a spinal stabilizer and the screw that is utilized to affix the stabilizer to the spinal column that allows the screw to be oriented at any of a plurality of angles relative to the plate so as to effectively transfer the load from the spinal column to the plate. The plate is provided with a hole comprised of an aperture, a central portion, and an opening, the head of the screw residing in the central portion of the hole when the screw extends through the hole into the vertebral body, the diameter of the aperture of the hole being smaller than the diameter of the head of the screw so that the head of the screw is retained in the hole through the plate.

The invention also contemplates a spinal stabilizer including such a multi-axis connection. The spinal stabilizer comprises a plate adapted to be affixed to a vertebra and having a plurality of holes formed therein, each hole defining an aperture, an opening, and a central portion between the aperture and the opening. The screw is comprised of a threaded shank and a threaded head, the shank of the screw extending into the body of the vertebra when the screw is rotated relative to the plate so that the thread on the head of the screw pulls the head of the screw through the aperture and into the central portion of the hole, thereby providing effective transfer of the load from the patient's spinal column to the spinal stabilizer regardless of the angle at which the screw is oriented relative to the plane defined by the aperture of the hole in the plate and locking the screw in the plate at the same time.

In another aspect, the present invention comprises a plate extending from one vertebra of the spine of a patient to an adjacent vertebra and having a plurality of holes therein, each hole being comprised of an opening, an aperture, and a central portion between the aperture and the opening, the diameter of the aperture being smaller than the diameter of the central portion of the hole and the diameter of the aperture also being smaller than the diameter of the central portion of the hole. A screw is received in the hole in the plate and is comprised of a head for engaging the plate and a threaded shank for screwing into the vertebra for affixing the plate to the vertebra. A thread is formed on the head of the screw for pulling the head of the screw through the aperture of the hole in the plate into the central portion of the hole when rotated relative to the plate, the head being retained in the central portion of the hole by the smaller diameter aperture and opening, thus locking the head into the hole in the plate and resisting movement of the screw relative to the plate.

The present invention also provides a method of transferring load from the vertebrae of a patient to the plate of a spinal stabilizer comprising the steps of approximating a plate to the surfaces of the vertebrae to be stabilized, driving a screw through a hole in the plate and into the vertebrae until the head of the screw contacts the plate at the margin of an aperture, the aperture, an opening, and a central portion between the aperture and opening defining the hole in the plate, the aperture and the opening being smaller in dimension than the head of the screw. After the screw contacts the plate at the margin of the aperture, the screw is rotated (relative to the plate) approximately one turn so that a screw thread formed on the head of the screw bites into the material comprising the plate at the margin of the aperture and pulls the head of the screw through the aperture and into the central portion of the hole in the plate. In the preferred embodiment, the central portion of the hole is larger in dimension than the head of the screw so that the screw can be positioned so as to extend from the plate at any of a plurality of angles relative to the plane defined by the aperture of the hole in the plate and the head of the screw can move freely in the central portion of the hole to accommodate the particular angle required at the interface between the screw and the plate while still being retained within the hole by the smaller diameters of the opening and the aperture of the hole.

The method of the present invention also contemplates removal of the screw from the hole in the plate by rotating the screw while pulling up on the screw head, pushing down on the plate, or by pulling up on the screw head while pushing down on the plate, so that the thread formed on the head of the screw bites into the material comprising the plate at the margin of the aperture and pulls the head of the screw up out of the hole through the narrow, or smaller diameter aperture so that the screw can then be backed out of the hole by the interaction of the threads and the vertebral body. A second screw, having a shank that is longer than the first, or a shank that is larger in diameter than the first, or both a shank that is longer than the shank of the first screw and a shank that is larger in diameter than the shank of the first screw, is then driven through the hole in the plate and into the vertebrae until the head of the second screw contacts the plate at the margin of an aperture. After the head of the second screw contacts the plate at the margin of the aperture, the second screw is rotated (relative to the plate) approximately one turn so that a screw thread formed on the head of the second screw bites into the material comprising the plate at the margin of the aperture and pulls the head of the second screw through the aperture and into the central portion of the hole in the plate with the shank of the second screw angled at any one of a plurality of angles relative to the plane of the aperture as may be necessary to effectively transfer load from the patient's spinal column to the plate. In the same manner that the first screw is locked into the hole to resist movement relative to the plate by the smaller diameter opening and aperture of the hole in the plate, the second screw is likewise locked into the hole in the plate.

DETAILED DESCRIPTION OF THE PREFERRED EMBODIMENTS

Figure 2:
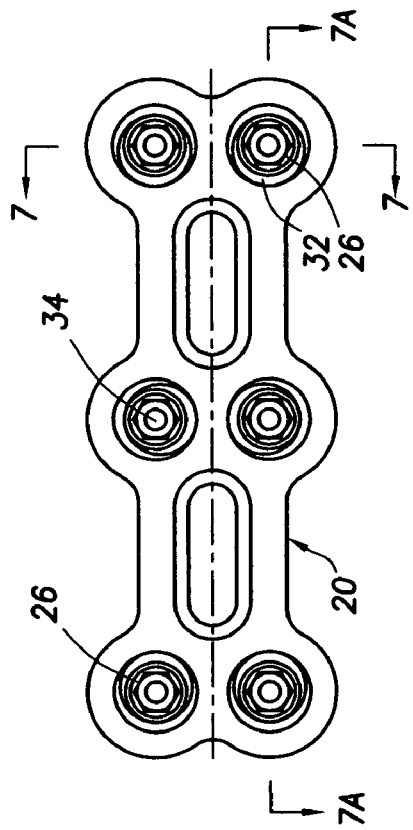
FIG. 2 is a plan view of a plate for a spinal stabilizer for stabilizing three adjacent vertebrae having screws comprising, together with the respective holes in the plate, a multi-axis connection constructed in accordance with the present invention received in the holes.
Figure 1:
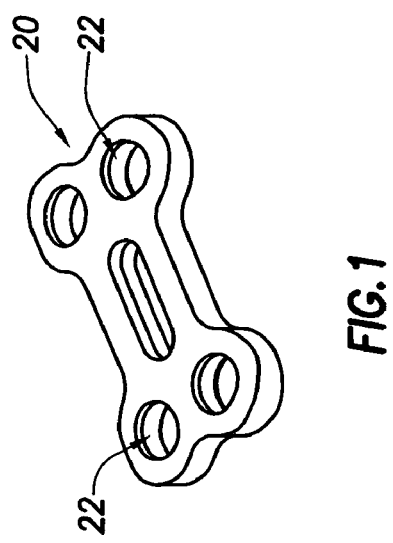
Referring to FIG. 1 of the drawings, there is shown a perspective view of a plate comprising a stabilizer incorporating a multi-axis connection constructed in accordance with the teachings of the present invention for use in stabilizing two adjacent spinal vertebrae.
Figure 3:
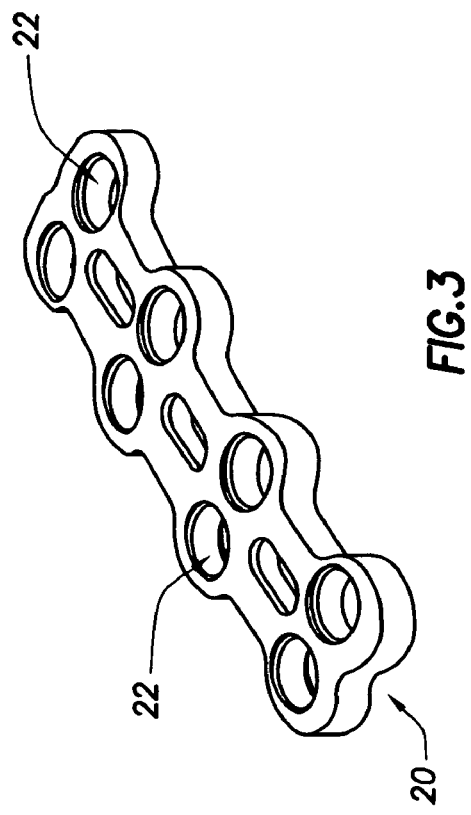
FIG. 3 is a perspective view of a plate for a spinal stabilizer comprising one component of a stabilizer incorporating a multi-axis connection constructed in accordance with the present invention for use in stabilizing four adjacent spinal vertebrae.

Referring now to FIGS. 1-3, a preferred embodiment of a plate comprising one component of a multi-axis connection for a spinal stabilizer constructed in accordance with the present invention is shown. The preferred embodiment of this plate, indicated generally at reference numeral 20, is provided with a plurality of holes 22 spaced along the length of the plate at locations corresponding to the spacing of the vertebrae of the spinal column of a patient (not shown) for receiving screws as shown in FIG. 2 at reference numeral 24 for screwing into the body of the respective vertebra to affix the stabilizer to the spine. The three plates 20 shown in FIGS. 1, 2, and 3 are sized, and define a corresponding number of holes 22, for stabilizing two, three, and four vertebrae, respectively. Although not shown very well in FIGS. 1-3, plate 20 is curved along its cross-sectional axis (see FIGS. 7, 7B, and 7C) and arched, or curved, along its longitudinal axis (see FIGS. 6 and 7A) so as to closely approximate the anterior surfaces of the vertebral bodies of the cervical vertebrae to which it is to be affixed; those skilled in the art will recognize that depending upon the location to which the plate 20 is to be affixed to the cervical spine, the particular pathology and anatomy of the patient, and other relevant factors, curvature(s) other than the curvature shown in the figures may be advisable for the plate 20.

Figure 4:
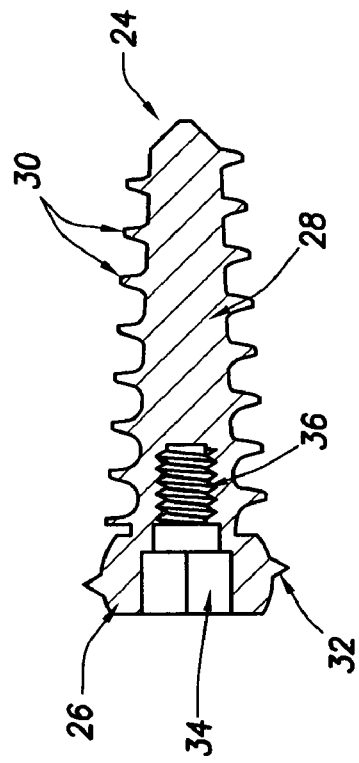
FIGS. 4 and 4A are longitudinal sectional and top plan views, respectively, of a preferred embodiment of a screw comprising one component of a multi-axis connection for a spinal stabilizer constructed in accordance with the teachings of the present invention.
Figure 4A:
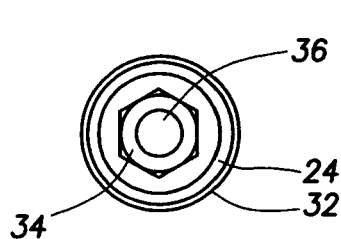

Referring now to FIG. 4, a presently preferred embodiment of a screw 24 for affixing the spinal stabilizer of the present invention to respective vertebral bodies of the spine of a patient is shown in longitudinal sectional view. Screw 24 is comprised of a head 26 and an elongate shank 28 with threads 30 along the length of the shank 28 for screwing screw 24 into the vertebral body of the vertebra. The head 26 is also provided with a screw thread 32 on the surface thereof which, in the preferred embodiment, extends only approximately a single turn around the circumference of head 26. A socket 34 opens to the top of the head 26 of screw 24 as best shown in FIG. 4A for receiving an Allen wrench, or hex key (not shown), of corresponding size for a purpose set out below. The socket 34 terminates in a left-hand threaded bore 36, the axis of bore 36 being coincident with the axis of socket 34, for a purpose also set out below.

Figure 6:
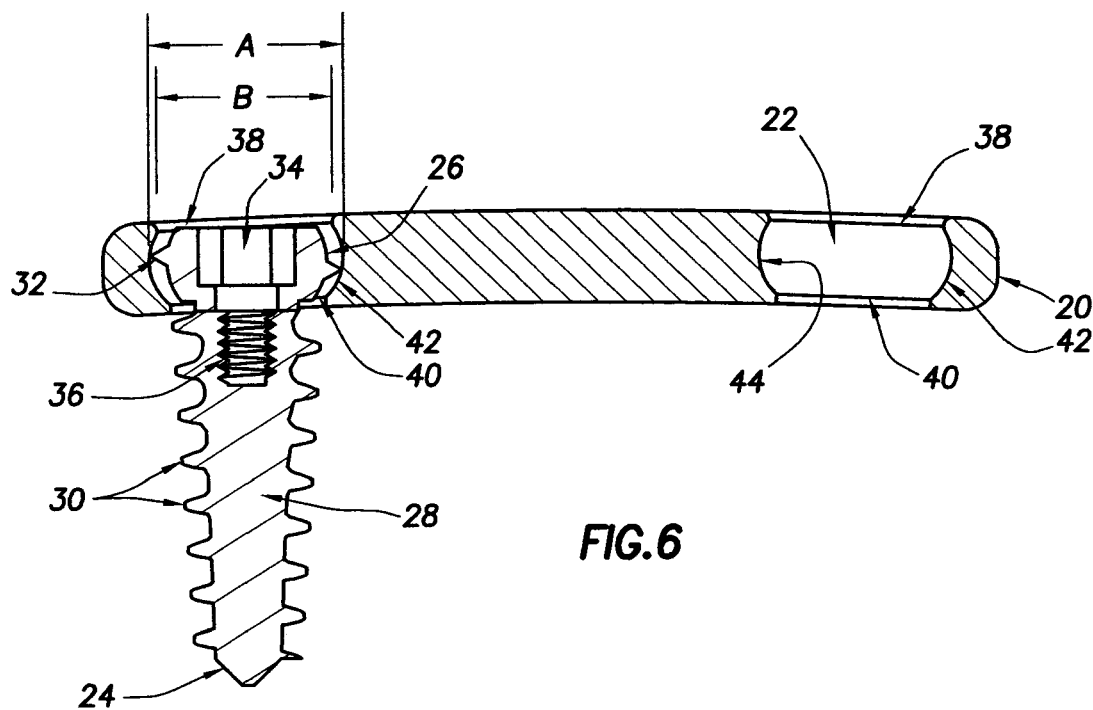
FIG. 6 is an sectional view of a plate such as the plate shown in FIG. 1 having the screw of FIG. 4 extending through a hole in the plate, enlarged to show the interaction between the head of the screw and the margins of the hole in the plate as well as the diameters of the component parts of the hole and the head of the screw.
Figure 7:
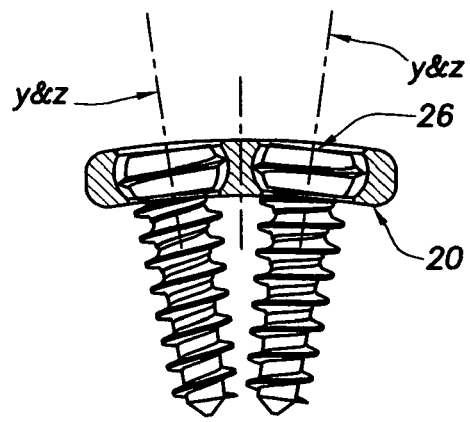
FIGS. 7, 7B, and 7C are cross sectional views taken along the line 7-7 in FIG. 2

Referring now to FIG. 6, the interaction between the head 26 of screw 24 and the holes 22 in plate 20 is shown in more detail. Each of the holes 22 in plate 20 is comprised of an aperture 38 on one side of plate 20 (referred to herein as the top of plate 20, but those skilled in the art that the word "top" is a relative term intended to denote direction and/or orient the user of the multi-axis connection of the present invention rather than to delimit or restrict the plate to a particular configuration or structure), an opening 40 at the bottom of plate 20 (the term "bottom" likewise being intended for the purpose or orienting the user rather than to require certain structure), and a central portion 42 between aperture 38 and opening 40. The walls, or margins, of the central portion 42 of hole 22 are concave as shown at reference numeral 44 so that the generally rounded, or hemispherically-shaped, head 26 of screw 24 resides in the rounded central portion 42 of hole 22 when the head 26 of screw 24 is rotated through the aperture 38 of the hole 22 in plate 20 as described below. As shown by reference lines A and B in FIG. 6, which correspond to the diameter of the head 26 of screw 24 and the diameter of the aperture 38 of hole 22, respectively, the diameter of the head 26 of screw 24 is slightly larger than the diameter of the aperture 38 into hole 22 (note that the thread 32 on head 26 is being included in the diameter A of the head 26 of screw 24) and, in the preferred embodiment, the plate 20 is comprised of a material that is capable of being cut through, or scored by, the material comprising screw 24 so that when the screw 24 is inserted into hole 22 and rotated relative to plate 20, the head 26 of screw 24 is pulled through aperture 38 on the thread 26 so that the head 26 resides in the central portion 42 of hole 22. Those skilled in the art will recognize that plate 20 may be comprised of a physiologically inert polymer, titanium, stainless steel, or other suitable material and that screw 24 may be comprised of a physiologically inert ceramic, polymer, metal, or metal alloy that is harder than the material comprising plate 20 so that the thread 32 on the head 26 of screw 24 "bites into" or cuts through the material comprising plate 20 for this purpose. Once the head 26 is positioned in the central portion 42 of hole 22, however, and also by reference to FIG. 6, it can be seen that the thread 32 no longer engages the margin of hole 22 and is therefore free to rotate and/or pivot relative to plate 20 while being retained in the central portion 42 of hole 22 by the smaller diameter aperture 38 and opening 42 of hole 22.

Figure 7A:
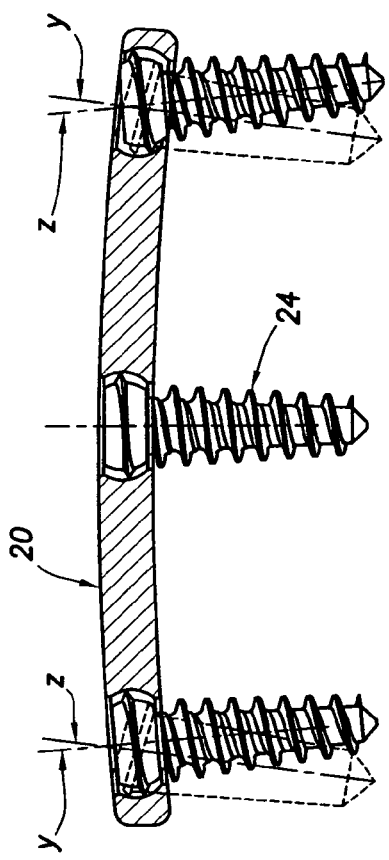
FIG. 7A is a longitudinal sectional view taken along the line 7A-7A in FIG. 2 showing how the head of the screw and the shape of the hole in the plate interact to allow the screw to be positioned at any of a plurality of angles relative to the plane defined by the aperture of the hole in the plate.
Figure 7C:
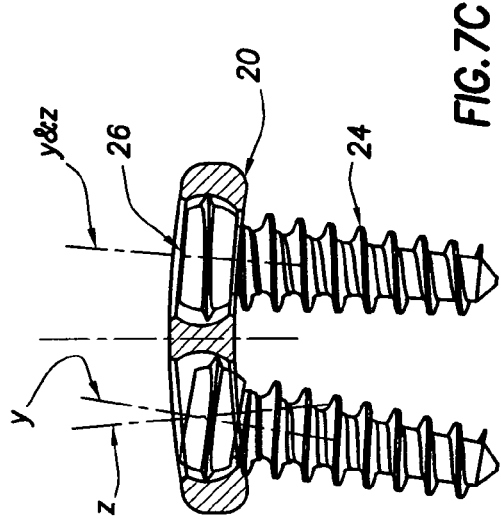
Figure 7B:
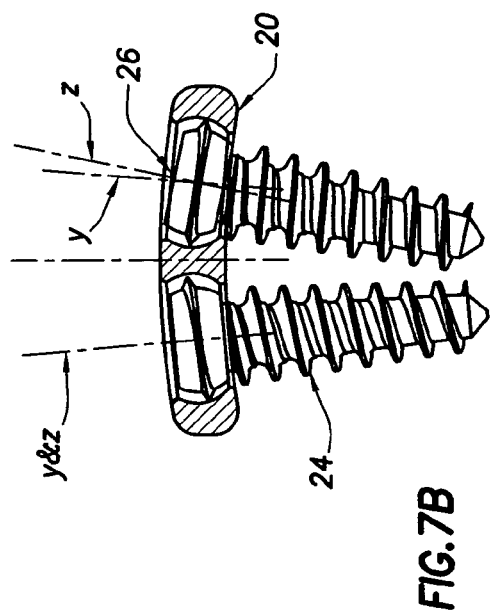

As noted above, the need for effective load transfer from the vertebrae of the patient's spine to the screws 24 in the vertebrae to plate 20, the lordosis of the spine, the need to angle the screws 24 inwardly (best shown in FIG. 7), the curvature of the plate along its longitudinal axis so that the plate closely approximates the surfaces of the vertebral bodies to which it is affixed (see FIG. 6), the need to angle the screws cranially and caudally so that the screws are positioned at optimal angles as the bone plug between disks sinks (as shown in FIG. 7A), the different sizes, spacing, and shapes of the vertebral bodies comprising the spine, and many other factors (including the particular pathology which the spinal fixation system is intended to address), require that almost every screw 24 be affixed to the body of the corresponding relative to plate 20. The above-described sizing of the head 26 of screw 24 relative to the central portion 42 of the respective hole 22 in plate 20 allows effective load transfer to plate 20 after the head 26 of screw 24 is pulled through the aperture 38 and into the central portion 42 of hole 22 such that the screw 24 can be positioned at any of a plurality of angles relative to the plane defined by the aperture 38 in plate 20 while still being constrained, or confined against movement relative to plate 20 by the smaller diameters of the aperture 38 and opening 40 of hole 22, thereby effectively locking the head 26 of screw 24 to plate 20 and transferring load from the vertebrae to plate 20. Referring to FIGS. 7, 7A, 7B, and 7C, the axis of the hole 22 through plate 20 is shown by reference line y. In more detail, line y represents an axis oriented at an angle of approximately 90° to the plane defined by the aperture 38 of hole 22. By referring to the figures, it can be seen that the axis y of hole 22 and the axis of screw 24, represented by reference line z, may be coincident or oriented at different angles relative to each other and that the angle between lines y and z may vary in different directions (compare the angle between y and z in FIG. 7A with the angle between lines y and z in FIGS. 7B and 7C). In the preferred embodiment, this angle between lines y and z may vary by up to as much as about 15° (the angles shown in the drawings are exaggerated for purposes of illustration), but those skilled in the art will recognize that the invention is not limited to this range of up to about 15° and that the angles that may need to be accommodated in a multi-axis connection constructed in accordance with the present invention may range up to as much as 30° or more.

Implantation of a spinal stabilizer incorporating the multi-axis connection of the present invention by anterior approach to the cervical spine is as follows. Once the anterior surface of the vertebral bodies has been exposed, the disk (or a portion of the disk) is removed, the adjacent vertebrae are distracted, and if a partial diskectomy is being performed, a bone plug (or other implant) is inserted into the intervertebral disk space. The vertebral bodies are evened out so that plate 20 closely approximates the anterior surfaces of the vertebral bodies when positioned thereon. Pilot holes are drilled in the vertebrae using the holes 22 in plate 20 as a template, screws 24 of appropriate sizes and diameters for the particular patient are selected, and the screws 24 are driven (using a hex key, or Allen wrench, sized to fit the socket 34 opening to the top of the head 26 of screw 24) into the vertebral bodies at the angle (relative to the plane defined by the aperture 38 of the hole 22 in plate 20) needed to effectively transfer load to plate 20. When a screw 24 has been driven into the respective vertebral body far enough that the head 24 contacts the margins of the aperture 38 of hole 22 through which the screw 24 extends, the screw is rotated approximately one rotation to cause the thread 32 on the head 26 to bite into the margins of the aperture 38 of hole 22 and pull the head 26 through the smaller diameter aperture 32 into the larger diameter central portion 42 of hole 22. Once the head 26 of screw 22 is positioned in the central portion 42 of hole 22, additional rotation of screw 24 (for instance, to tighten plate 20 against the surfaces of the vertebral bodies) does not change the relative angle or position between plate 20 and screw 24. Stated another way, once the head 26 of screw 24 is positioned in the central portion 42 if the hole 22 in plate 20 and because the head 26 of screw 24 is of smaller diameter than the diameter of the central portion 42 of hole 22, plate 20 and head 26 of screw 24 do not change position or angle relative to each other when the screw 22 is rotated relative to plate 20 because the thread 32 on the head 26 of screw 24 does not contact the concave side walls 44 of the central portion 42 of the hole 22 in plate 20 (and, as set out above, the screw 24 is free to rotate or pivot relative to plate 20 while being retained in the central portion 42 of hole 20).

Figure 5:
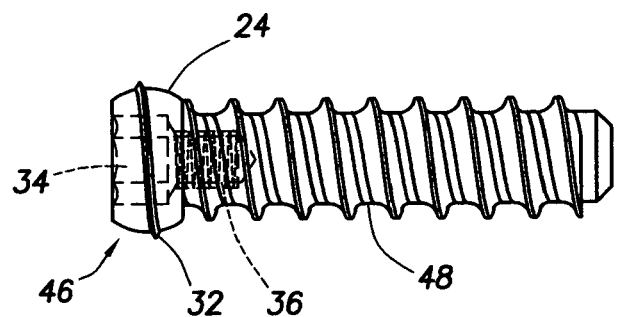
FIG. 5 is a side elevational view of a second preferred embodiment of a screw comprising one component of a multi-axis connection for use in connection with a spinal stabilizer constructed in accordance with the teachings of the present invention.

As noted above, sizing and placement of a stabilizer is part of the skill involved in an implantation that effectively transfers load from spinal column to stabilizer, but there are times when implantation is a matter of trial and error. In such surgeries, it may be necessary to replace a screw that is, for instance, found to be too short to successfully transfer load after it has already been driven into the vertebral body. However, the nature of the bone comprising the vertebral body is such that a screw that is found to be too short cannot simply be replaced by a longer screw. Instead, the first screw must be replaced with a second screw with a shank that is longer, larger in diameter, or both longer and larger in diameter than the first screw. A screw that is appropriate for use as a replacement (second) screw for the multi-axis connection of the present invention is shown at reference numeral 46 in FIG. 5. The need for a larger diameter replacement screw is fulfilled in the case of screw 46 by utilizing a straight threaded shank 48 rather than the tapered threaded shank 28 of screw 24 shown in FIG. 4.

Of course as noted above, rotation of screw 24 relative to plate 20 after the head 26 of screw 24 is pulled through aperture 38 by the thread 32 formed on the head 26 of screw 24 does not cause relative movement between plate 20 and screw 24 such that it would appear that replacement of a screw that is too short for effective load transfer would be problematical. This problem, however, is addressed by screwing a probe (not shown) with a left-hand thread formed on the end thereof sized to bottom out in the left-hand threads of the bore 36 opening to the head 26 of screw 24 to cause left-hand rotation of the screw 24 to back screw 24 out of the vertebral body. Either by exertion of upward (pulling) force on screw 24, downward force on the surface of plate 20, or a combination of upward (pulling) force on screw 24 and downward force on plate 20, during left-hand rotation with the probe, the thread 32 on the head 26 of screw 24 is caused to bite into the material comprising plate 20 at the margin of the aperture 38 of hole 22 to rotate the head 26 up out of the hole 22 in a manner opposite the manner in which the head was rotated through the aperture 38 into the central portion 42 of opening 22. Once head 26 emerges from aperture 38, screw 24 is backed out of the vertebral body by rotation of the probe and subsequently replaced by inserting second screw 46 into the hole 22 in plate 20 and driving second screw 46 into the vertebral body in the same manner as described above for screw 24. When the head 26 of second screw 46 contacts the margins of the aperture 38 of hole 22, the screw 46 is rotated approximately one turn to cause the thread 32 on the head 26 of second screw 46 to bite into the material comprising plate 20 to pull the head 26 into the larger diameter central portion 42 of opening 22 and to lock the head 26 of second screw 46 into the hole 22 to resist movement of plate 22 relative to screw 46 in the same manner described above in connection with the placement of (first) screw 24.

Although described in terms of the presently preferred embodiment shown in the figures, those skilled in the art will recognize that changes can be made to the component parts of the present invention without changing the manner in which those component parts function to achieve their intended result. For instance, although described herein as being part of an internal spinal stabilizer implanted with an anterior approach to the cervical spine, the multi-axis connection of the present invention is equally adaptable to a spinal fixation system comprised of rods and plates, or cross-bars, that is affixed to other portions of the spinal column by dorsal approach to the spinal column with the screws that are retained, or locked, in the holes formed in the plates being driven into the pedicles of the respective vertebrae at any of a plurality of angles relative to the planar aperture of the openings as required for proper placement of the stabilizer and effective load transfer from the spinal column to the stabilizer. It will also be recognized from the disclosure set out herein by those skilled in the art that the head of the screw, although shown in the figures as being substantially round, or hemispherically-shaped, may be formed in a frustoconical, oval, or ellipsoidal shape, all of which will achieve the purpose of interacting with the margins of hole 22 in the manner described herein to effectively transfer load at a plurality of angles of the screw relative to planar aperture 38 while resisting movement relative to the plate 20. All such changes, and the others known to those skilled in the art, are intended to fall within the scope of the following non-limiting claims.

What is claimed is:

1. A spinal stabilizer comprising:
   a plate, the plate being provided with at least one hole there through, the hole defining an aperture at the top of the plate and an opening at the bottom of the plate, the aperture and the opening connected by a contiguous central portion of the hole, the central portion of the hole defining an unobstructed cavity with concave side walls, and
   at least one screw, the screw comprising a rounded head and a threaded shank coupled to the rounded head, the rounded head having a single thread extending approximately a single turn around the circumference of the head of the screw, the diameter of the threaded screw head is greater than the diameter of the aperture, and further the diameter of the threaded screw head is greater than the diameter of the opening,
   the diameter of the central portion of the hole is large enough that the thread on the rounded head of the screw does not contact the concave side walls of the central portion of the hole such that the threaded screw head is free to rotate relative to the plate while being retained in the unobstructed cavity of the central portion of the hole by the smaller diameters of the aperture and the opening of the hole, and
   the screw adapted to be inserted at an angle relative to the plane defined by the aperture of the hole in the plate.

2. The spinal stabilizer of claim 1 further comprising a wrench socket opening to the top of the head of the screw for receiving either an Allen wrench or a hex key, the Allen wrench or hex key sized to fit the wrench socket.

3. The spinal stabilizer of claim 2 wherein the wrench socket comprises a bore having an axis coincident with the opening to the top of the head of the screw and having a left-hand thread formed therein for locking into the head of the screw to facilitate backing the screw head out of the aperture.

4. A spinal stabilizer comprising:
   a plate, the plate being provided with at least one hole there through, the hole defining an aperture at the top of the plate and an opening at the bottom of the plate, the aperture and the opening connected by a contiguous central portion of the hole, the central portion of the hole defining an unobstructed cavity with concave side walls, and
   at least one screw, the screw comprising a head and a threaded shank, the head having a thread extending approximately a single turn around the circumference of the head of the screw so that the thread on the head of the screw is suitable for biting into the plate at a margin of the aperture when the screw is rotated approximately one rotation relative to the plate to reside in the central portion of the hole, the diameter of the threaded screw head is greater than the diameter of the aperture, and further the diameter of the threaded screw head is greater than the diameter of the opening, the diameter of the central portion of the hole is large enough that the thread on the head of the screw does not contact the concave side walls of the central portion of the hole such that the threaded screw head is free to rotate relative to the plate while being retained in the unobstructed cavity of the central portion of the hole by the smaller diameters of the aperture and the opening of the hole, and the screw is adapted to be driven into vertebral bodies at an angle relative to the plane defined by the aperture of the hole in the plate.

5. The spinal stabilizer of claim 4 additionally comprising a socket opening to the top of the head of the screw for receiving either an Allen wrench or a hex key, the Allen wrench or hex key sized to fit the socket, for rotating the head of the screw.

6. The spinal stabilizer of claim 5 further comprising a bore having an axis coincident with the opening to the top of the head of the screw and having a left-hand thread formed therein to facilitate backing the screw head out of the aperture.

7. The spinal stabilizer of claim 4 further comprising a multi-axis connection between the screw and the plate for stabilizing the vertebrae of the spinal column of a patient, the threaded screw head residing in the central portion of the hole with the threaded shank extending through the opening of the hole at any of a plurality of angles relative to the plane defined by the aperture of the hole in the plate.

8. The spinal stabilizer of claim 7 wherein the diameter of the central portion of the hole in the plate is large enough relative to the threaded screw head that the threaded screw head pivots with respect to the plate when the threaded screw head is retained in the central portion of the hole in the plate.

9. The spinal stabilizer of claim 4 wherein the diameter of the central portion of the hole in the plate is large enough relative to the threaded screw head to allow the screw to change angles with respect to the plate when the threaded screw head is positioned in the central portion of the hole in the plate.

10. A method of transferring load from the vertebrae of the spinal column of a patient to a spinal stabilizer affixed to the vertebrae, the spinal stabilizer comprising a plate and a screw, comprising:

approximating the plate of the spinal stabilizer to a surface of the vertebrae to be stabilized;

driving a screw through a hole in the plate and into the vertebrae until a head of the screw contacts the plate at a margin of an aperture, the hole defining the aperture at the top of the plate and an opening at the bottom of the plate, the aperture and the opening connected by a contiguous central portion of the hole, the central portion of the hole defining an unobstructed cavity with concave side walls, the screw comprising the head and a threaded shank, the head having a thread extending approximately a single turn around the circumference of the head of the screw, the diameter of the threaded screw head is greater than the diameter of the aperture, and further the diameter of the threaded screw head is greater than the diameter of the opening, the screw driven into the vertebrae at an angle relative to the plane defined by the aperture of the hole in the plate, and after the screw contacts the plate at the margin of the aperture, rotating the screw approximately one rotation so that the thread formed on the head of the screw bites into the material comprising the plate at the margin of the aperture, the diameter of the central portion of the hole is large enough that the thread on the head of the screw does not contact the concave side walls of the central portion of the hole such that the threaded screw head is free to rotate relative to the plate while being retained in the unobstructed cavity of the central portion of the hole by the smaller diameters of the aperture and the opening of the hole.

11. The method of claim 10 additionally comprising removing the screw from the hole in the plate by rotating the screw either while pulling up on the screw, pushing down on the plate, or pulling up on the screw and pushing down on the plate, the screw removed using a probe.

12. The method of claim 11 additionally comprising replacing the first screw with a second screw having a shank that is either longer, larger in diameter, or both longer and larger in diameter than the shank of the first screw.

* * * * *